United States Patent [19]

Sibalis

[11] Patent Number: 4,708,716
[45] Date of Patent: Nov. 24, 1987

[54] TRANSDERMAL DRUG APPLICATOR

[75] Inventor: Dan Sibalis, Stony Brook, N.Y.

[73] Assignee: Drug Delivery Systems Inc., New York, N.Y.

[21] Appl. No.: 778,183

[22] Filed: Sep. 16, 1985

Related U.S. Application Data

[63] Continuation-in-part of Ser. No. 524,252, Aug. 18, 1983, Pat. No. 4,557,723, and a continuation-in-part of Ser. No. 660,192, Oct. 12, 1984, Pat. No. 4,622,031.

[51] Int. Cl.$^4$ .............................................. A61N 1/30
[52] U.S. Cl. ...................................... 604/20; 604/892;
128/635; 128/640; 128/798
[58] Field of Search ............... 128/635, 639, 640, 783, 128/798, 799; 604/20, 891, 892, 896; 204/299 R, 301

[56] References Cited

U.S. PATENT DOCUMENTS

| | | | |
|---|---|---|---|
| 385,567 | 7/1888 | Hoke | 403/68 |
| 486,902 | 11/1892 | Shultz | 604/20 |
| 588,479 | 8/1897 | Roedel | 604/20 |
| 2,493,155 | 1/1950 | McMillan | 604/20 |
| 2,667,162 | 1/1954 | Zwahlen | 604/20 |
| 2,784,715 | 3/1957 | Kestler | 604/20 |
| 3,163,166 | 12/1964 | Brant et al. | 604/20 |
| 3,289,671 | 12/1966 | Troutman et al. | 604/20 |
| 3,547,107 | 12/1970 | Chapman et al. | 128/640 |
| 3,612,061 | 10/1971 | Collins | 128/799 |
| 4,003,379 | 1/1977 | Ellinwood, Jr. | 604/891 |
| 4,008,721 | 2/1977 | Burton | 128/802 |
| 4,141,359 | 2/1979 | Jacobsen et al. | 604/20 |
| 4,164,226 | 8/1979 | Tapper | 128/798 |
| 4,239,046 | 12/1980 | Ong | 128/798 |
| 4,243,052 | 1/1981 | Bailey | 128/798 |
| 4,250,878 | 2/1981 | Jacobsen et al. | 604/20 |
| 4,273,135 | 6/1981 | Larimore et al. | 128/802 |
| 4,292,968 | 10/1981 | Ellis | 604/20 |
| 4,309,996 | 1/1982 | Theeuwes | 604/892 |
| 4,314,554 | 2/1982 | Greatbatch | 604/20 |
| 4,325,367 | 4/1982 | Tapper | 128/803 |
| 4,367,745 | 1/1983 | Welage | 128/303.13 |
| 4,406,658 | 9/1983 | Lattin et al. | 604/20 |
| 4,416,274 | 11/1983 | Jacobsen et al. | 604/20 |
| 4,419,091 | 12/1985 | Behl et al. | 604/20 |
| 4,457,748 | 7/1984 | Lattin et al. | 604/20 |
| 4,460,368 | 7/1984 | Allison et al. | 604/896 |
| 4,474,570 | 10/1984 | Ariura et al. | 604/20 |

FOREIGN PATENT DOCUMENTS

| | | | |
|---|---|---|---|
| 2500689 | 8/1982 | France . | |
| 8102097 | 8/1981 | World Int. Prop. O | 128/640 |
| 2104388 | 3/1983 | United Kingdom . | |

OTHER PUBLICATIONS

"The Enzyme Electrode", by Updike et al., *Nature*, vol. 214, Jun. 3, 1967, pp. 986–988.

Primary Examiner—Lee S. Cohen
Assistant Examiner—Randy Citrin
Attorney, Agent, or Firm—Lackenbach Siegel Marzullo & Aronson

[57] ABSTRACT

A transdermal drug applicator for application to a body for the migration of medicament through the skin into the blood stream of a patient embodies a plurality of reservoirs for containing the medicament. A battery which supplies a charge for the medicament in the applicator is disposed adjacent one side of the reservoirs with a side of the battery facing the reservoir for charging/driving the medicament. Also, a cover comprising an electrically conductive material partially encloses the battery and one side of the reservoir opposite that of the battery is exposed for contacting the skin. An electrical circuit is further provided for electrically connecting the battery to the cover, and the cover having a lip defining the periphery of the applicator for making contact with the skin when mounted on the skin leaving the battery and reservoir generally fully enclosed. An electrically conductive adhesive material coating is disposed on the underside of the lip, said reservoir renders the applicator conformable to the body contours of the patient, and when the applicator is adhered to and mounted on the skin a complete electrical circuit through the skin is formed and the medicament in the reservoir migrates out of the reservoir and through the skin into the patient's blood stream.

24 Claims, 16 Drawing Figures

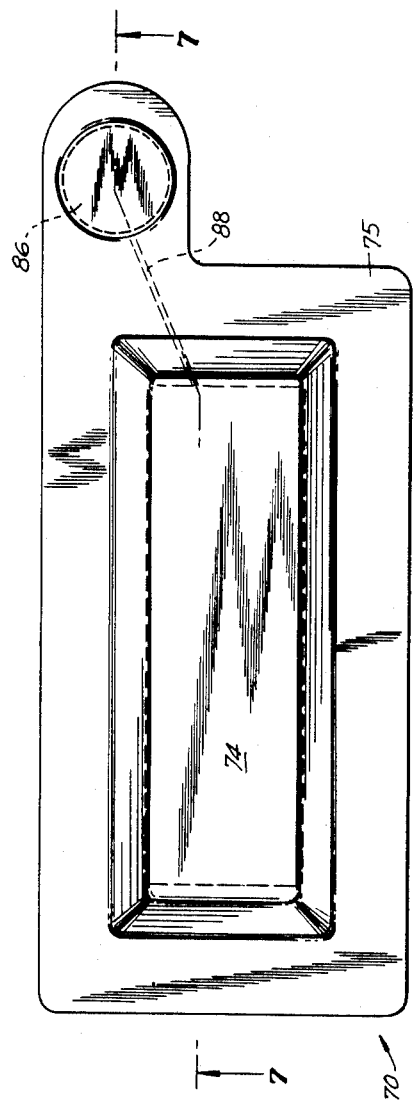
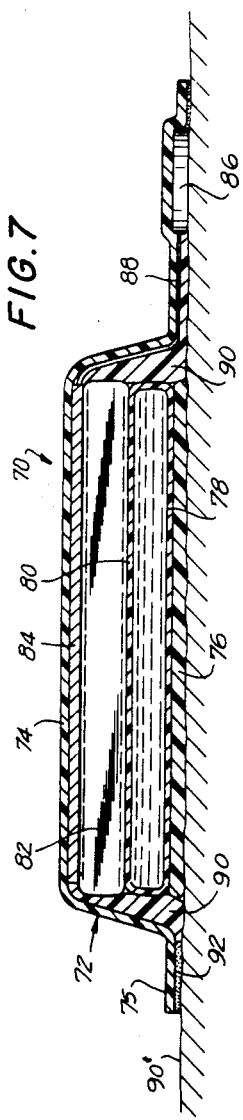
FIG. 6
FIG. 7

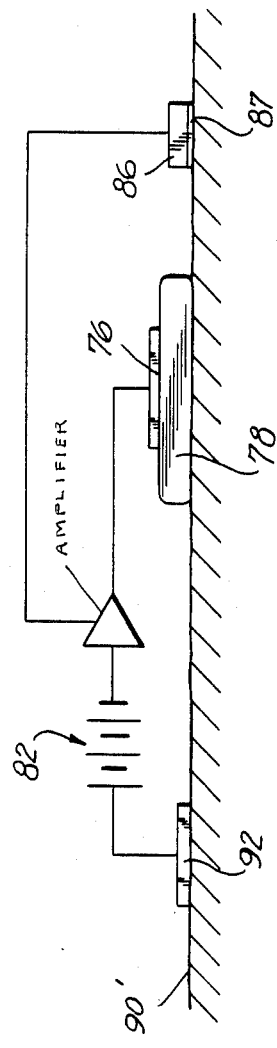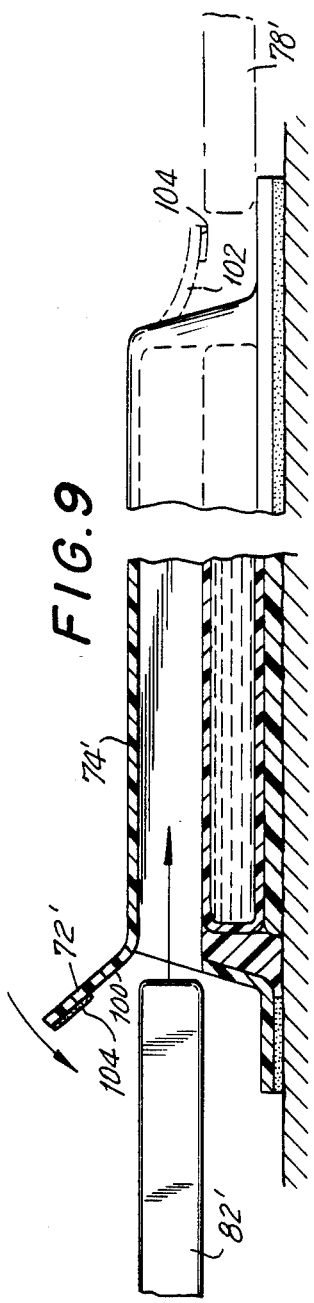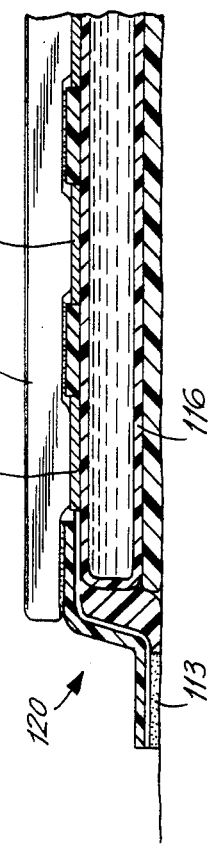

FIG. 14
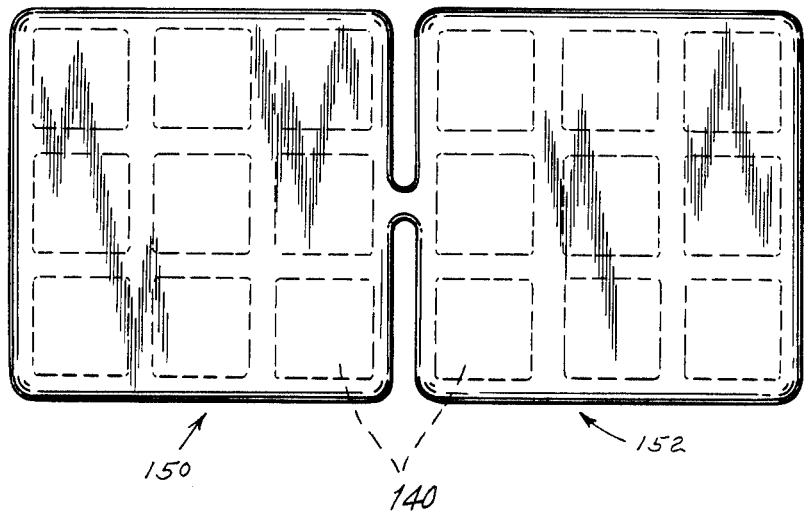
FIG. 15
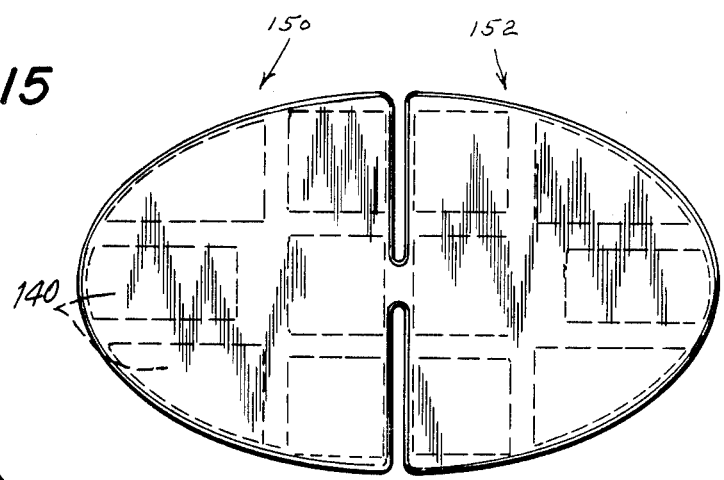
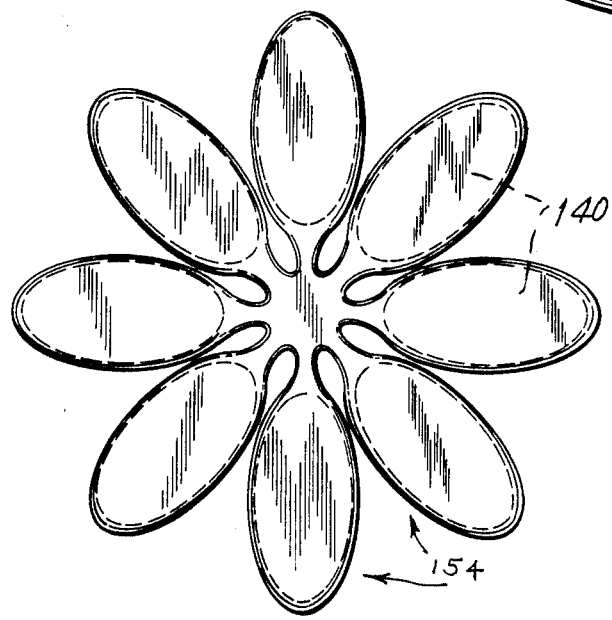
FIG. 16

TRANSDERMAL DRUG APPLICATOR

RELATED U.S. PATENT APPLICATIONS

This application is a continuation-in-part of my earlier filed U.S. patent applications, Ser. No. 524,252, U.S. Pat. No. 4,557,723 filed Aug. 18, 1983; and Ser. No. 660,192, U.S. Pat. No. 4,622,031 filed Oct. 12, 1984.

The invention disclosed and claimed in this patent application is a continuation-in-part of my earlier filed U.S. patent applications, Ser. No. 524,252 filed Aug. 18, 1983 (now U.S. Pat. No. 4,557,723); and Ser. No. 660,192; filed Oct. 12, 1984 (Now U.S. Pat. No. 4,622,031) and is also based upon PCT/US85/00080, filed Jan. 17, 1985, all of which priority is hereby based upon and claimed under 35 U.S.C. 120 for the two earlier filed U.S. cases and under the Patent Cooperation Treaty with respect to the PCT case.

FIELD OF THE INVENTION

This invention relates to electrophoretic and/or electro-osmosis transcutaneous drug delivery. Specifically, this invention relates to a self-contained applicator for the transdermal drug delivery of medication. More particularly, such an applicator construction includes specialized structural configurations that compensate for skin stretch and movement, thus preventing loosening of the applicator and minimizing the chance of "burns" or other "tingling" sensations should wider fluctuations of current density occur; and one in which a third electrode is employed to regulate the pumped drug in accordance with a signal fed back into an amplified circuit.

BACKGROUND OF THE INVENTION

The delivery of medicament through a person's skin utilizing electrophoresis and/or electro-osmosis is one where the drug molecules in solution or suspension are made subject to an electric field, and in the case of electrophoresis, if the electrode having the same charge as that of the ionic molecules is above the solution adjacent the skin which is the site of administration, the ions will be repelled and migrate through the skin into the blood stream; whereas in the case of electro-osmosis, a solution of water is attracted to the negative electrode, and thus any electric current flowing through a porous membrane causes a flow therethrough. Such electrochemical processes, although similar in end result do, however, function together, but separately or independently, in pumping and/or delivering a drug or other medication transdermally.

A variety of problems associated with these techniques have limited severely the extent of the use of such apparatus. Reference to or disclosure of such devices are shown in the following U.S. Patents, where it will be noted that there is great emphasis in developing electrodes which are disposable and/or more effective: U.S. Pat. Nos. 2,493,155, 3,163,166, 3,289,671, 3,677,268, 4,141,359, 4,166,457, 4,239,052, 4,243,052, 4,250,878, 4,273,135, 4,367,745.

It will be noted from U.S. Pat. Nos. 3,289,671 and 4,141,359, in particular, that the rate of drug delivery is a function of current flow and that control over current flow is crucial to having the correct amount of medicament applied.

There have also been attempts to provide an apparatus for such electrotherapy which is self-contained, so that the patient can wear the device carrying on normal activities while the drug is being administered. Devices of this type are disclosed in U.S. Pat. Nos. 385,556 to Hoke, 486,902 to Shultz, and 2,784,715 to Kestler.

The following U.S. patents are also of additional interest in connection with this application. U.S. Pat. Nos. 588,479, 2,667,162, 3,547,107, 4,008,721, 4,239,046, 4,325,367, 4,419,019.

Thus, for example, U.S. Pat. No. 588,479 to Roedel discloses an electric herb containing pad which provides simultaneous electrical and herbal applications to the body.

U.S. Pat. No. 2,667,162 to Zwahlen discloses a stocking with a battery connected to electrode pads formed with the stocking. The device is used for ionization of blood circulatory conditions in the lower limbs.

U.S. Pat. No. 3,547,107 to Chapman et al shows a self-contained chest mounted heart tachycardia detector, and an insertable replaceable battery is disclosed, and the device is held to the patient by a separate piece of tape.

U.S. Pat. No. 4,008,721 to Burton discloses a tape electrode per se for transmitting electrical signals through the skin. A silver metal containing electrically conductive layer is disposed over an adhesive layer.

In U.S. Pat. No. 4,325,367 to Tapper, there is disclosed a iontrophoretic treatment device which is self-contained in a fixed structural housing. Metal electrodes, particularly a stainless steel cathode and an aluminum anode are connected to respective adjacently mounted porous moisture absorbent pads, and are wire-connected to a battery. The device is not adhered to the user's body, but rather the user physically holds the device in place against the body.

U.S. Pat. No. 4,419,091 to Behl et al discloses an ion treatment electrode per se having a porous polymer substance with a conductive coating.

U.S. Pat. No. 3,163,166 to Brant et al discloses an iontophoresis device in a fixed interfitting structural housing, which is designed to be hand held in operation.

U.S. Pat. No. 2,493,155 to McMillan discloses an iontophoretic device which is strapped or taped to the body. The device is electrically operatively connected to an external controlled circuit source.

U.S. Pat. No. 4,239,046 to Ong is directed to an iontophoretic electrode construction per se including electrically conductive respective hook and knitted filaments for attachably detachable electrode connection.

U.S. Pat. No. 4,273,135 to Larimore et al is directed to a biomedical electrode per se in which the conductive material is formed of a cohesive, conformable, non-ionic hydrophilic synthetic polymer, so as to provide an essentially dry electrode.

U.S. Pat. No. 4,243,052 to Bailey is directed to a disposable electrode per se which combines a fabric backing and a conductive mesh layer laminated thereto, and a conductive polymer adhesive which interfaces the conductive mesh and which contacts the skin of the patient.

Also, U.S. Pat. No. 4,367,745 to Welage relates to an electrically polymeric conductive composition per se for interfacing between the skin and the electrode plate of a biomedical electrode.

None of the above-referenced devices disclose an electrophoretic and/or electro-osmosis bandage or applicator for the non-invasive transcutaneous delivery of a medicament which is a self-contained, self-adhering unit, in which the combination of elements including battery, a current regulating source, a medicament solution or reservoir, and an adhesive conductive lip are integrally connected by means of a flexible polymeric electrically conductive cover. Additionally, there is no teaching of an applicator or bandage-like transdermal drug delivery system in which specialized structural configurations compensate for one's movement and skin stretch so as to preclude loosening or "hot spots", or of incorporating a third or feedback electrode in the patch or applicator for regulating the drug dosage.

Other problems with such prior art devices were that they were bulky and lacked the necessary drug delivery rate control.

Another significant problem associated with such prior art devices is that the user, in wearing the device over the course of a few days caused the applicator patch to fall off because of one's movement during the day or by showering, perspiration, etc. These prior art devices did not provide for any structures which compensated for one's body movement, nor did they preclude the "peeling" effect. Moreover, no control means was provided for the regulation of administering the drug.

SUMMARY OF THE INVENTION

The present invention therefore overcomes or reduces many of the drawbacks of the previous devices and methods for utilizing electrophoresis and/or electroosmosis for the non-invasive transcutaneous delivery of a medicament.

This is accomplished in accordance with the principles of this invention by enclosing a complete electrophoretic and/or electro-osmosis drug administration system within an applicator virtually indistinguishable when in place from an adhesive bandage. The applicator is extremely shallow, capable of being made with a thickness of only about a tenth of an inch, and its length and width would be determined by the desired rate of drug delivery.

Preferred embodiments of this invention consists of a compact, multilayered applicator having unique "cellular-like" configurations, and having a first active layer containing medicament in contact with the skin, a second active layer superimposed on the first layer comprising a member to make electrical contact with the skin through the first layer, and a third active layer superimposed on the second layer comprising the electrical battery for the applicator in electrical contact with the second layer. Other layers may be included to provide other functions to be described. The applicator assembly is enclosed within a cover of electrically conductive material having a lip extending outwardly from the first layer and leaving the latter exposed and in contact with the skin. The underside of the lip is coated with an electrically conductive adhesive material so that when the applicator is mounted on the skin the cover material surrounded by the lip is in contact with the skin. The lip acts as a return electrode so that the skin completes the electrical circuit when the applicator is applied causing current to flow and medicament to be moved through the skin into the blood stream. A third electrode may be employed in a "loop" circuit to feedback a signal indicating when a desired dosage level is achieved in the blood serum, so that with such feedback loop a demand type applicator patch is achieved which regulates the drug dosage as desired. Also, an LCD or an electrochemically phototropic material (ECM) is incorporated in the circuitry of the device to serve as an indicator. With completion of the circuit, the indicator is activated so as to provide a positive indication that the drug is being delivered transdermally.

All the layers of the applicator may be made from conformable material so that the applicator is capable of being made large enough to be mounted over wide areas regardless of the contour involved.

Features which may be included in the applicator as described above include discrete cell construction, control electrode or probe and feedback loop circuit, a constant current flow limiting device and a device to terminate drug delivery after a predetermined period of time or quantity of drug.

It is thus a principal object of this invention to provide self-contained apparatus for the electrophoretic and/or electro-osmosis deposition of a medicament at a controlled rate.

Other objects and advantages of this invention will hereinafter become obvious from the following description of the preferred embodiments of this invention.

BRIEF DESCRIPTION OF THE DRAWINGS

FIG. 6 is a plan view of an alternate applicator similar to that of FIGS. 1 and 2, but incorporating a third or feedback electrode;

FIG. 7 is a sectional view taken along the line 7—7 of FIG. 6, and showing the applicator mounted on skin;

FIG. 8 is an electrical schematic of the circuitry embodying the third or feedback electrode and applicator shown in FIGS. 6-7;

FIG. 9 is an alternate applicator package construction wherein the battery and/or the medicament reservoir or pouch/pad containing the drug is inserted in the field at time of application to ensure freshness and longer life;

FIG. 10 is another modified construction wherein the battery is externally mounted to the applicator packages;

DESCRIPTION OF THE PREFERRED EMBODIMENTS

Figure 1:
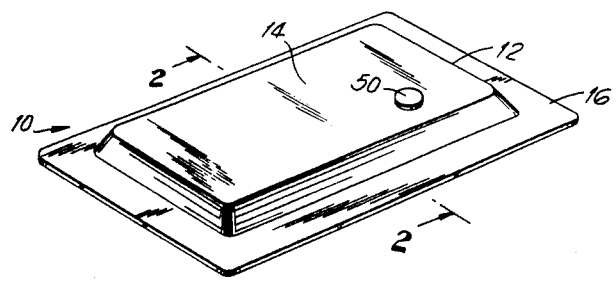
FIG. 1 is an isometric view of an applicator embodying the principles of this invention.
Figure 2:
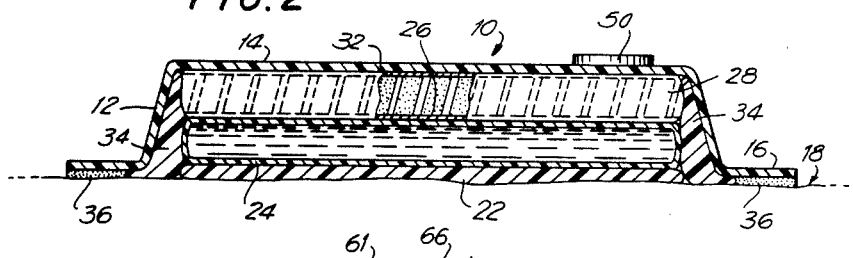
FIG. 2 is a cross-sectional view taken along the line 2—2 of FIG. 1, and showing the applicator mounted on skin.

Referring to FIGS. 1 and 2, applicator 10 consists of an outer cover 12 having a raised portion 14 and a lip 16 along the outer periphery. It is understood that applicator 10 can have any convenient shape or size, for example, square, rectangular, oval, circular, or tailored for a specific location on the skin, as long as this is a raised central portion to accommodate the rest of the electrophoresis and/or electro-osmosis unit to be described and the lip along its periphery.

As seen in FIG. 2, where applicator 10 is mounted on the surface of skin 18 of a patient, enclosed within the raised portion 14 of cover 12 are several layers to be described. The first layer is a microporous or semipermeable membrane 22 through which the medicament migrates to be deposited on skin 18. As will be noted from the following discussion, membrane 22 may not be needed, depending on the nature of the reservoir for the medicament.

The second layer consists of a flexible pad, pouch or other type reservoir 24 containing the drug to be administered. As is understood in the art, and shown in one or more of the U.S. patents identified above, reservoir 24 can be an impregnated pad or a pouch containing the drug of choice in solution or suspension, the walls of which are sufficiently dense to prevent leakage of the drug under ambient conditions, but sufficiently porous to permit migration of the drug, such as, for example, the charged particles or ions under the influence of the electric field imposed when utilizing electrophoresis. It should be noted that it would be appropriate to employ the microporous membrane 22 when leakage under ambient conditions could occur, for example, as a result of packing of the applicators for shipment or storage, fluctuating temperatures, and possibly puncture of the reservoir. Also, the use of the membrane 22 could depend in large measure on the nature of the medicament involved. In the alternative, reservoir 24 can consist of porous material in which the drug is impregnated rather than a pouch containing the liquid medicament.

The third or next layer above reservoir 24 is an extended contact 26 which could be incorporated as one face of battery 28 which is the next layer. Contact 26 could be any suitable conductive material, preferably body-conformable, to permit applicator 10 so as to be curved or bent to conform to the shaped surface of the skin. Suitable materials of this type are well known in the art and include electrically conductive polymers, preferably non-ionic. Carbon loaded or surface metalized plastic are also available for such use.

Battery 28 comprising the next layer can be made up of a group of cells internally connected in series to obtain the desired voltage necessary to obtain the electrophoretic action with the particular medicament, and orientation of battery 28 would depend on whether the charged (ionic) particles of the drug of choice are positive or negative. If the particles are negatively charged in solution or suspension, then contact 26 would be connected to the negative side of battery 28 as the skin will then be positive with respect to that contact and will attract the ions. With electro-osmosis, greater flexibility in design and structure is permissible as, for example, the pH of the drug solution is not important, since electro-osmosis is a physical phenomena, rather than a chemical phenomena. Moreover, the solution can be highly concentrated which is in contrast to that of an ionic solution, which requires high ion mobility and thus lower concentrations. However, with an entirely electro-osmosis unit, control of drug delivery is more difficult. Consequently, although both types of drug delivery systems are contemplated herein and come within the scope of this invention, the system utilized should be based upon drug chosen.

Both systems are combinable or can be used simultaneously to maximize the efficiency of the product or to make it possible to deliver non-ionic drugs and/or large rates of delivery.

With regard to battery 28, it should be noted that any conventional miniaturized battery cells now generally available can be employed, arranged and connected in series to obtain the desired operating voltage. In addition, the technology now exists for batteries which are made up of very thin, flexible sheets of a conductive polymer with high surface areas relative to thickness to provide adequate current densities. One such so-called plastic battery is described in "Batteries Today", Autumn 1981, pages 10, 11 and 24. When such a battery is employed, sheets may be layered to place the cells in series, and an effective compromise between number of sheets and surface areas of sheets is to layer them in a diagonal as shown somewhat schematically in FIG. 2. Of course, battery selection would ultimately depend on such factors as the degree of conformability desired, voltage and current densities required for a specific application, and time to discharge.

Layered above battery 28 would be another contact 32 which could be similar in construction to that of contact 26 and connected electrically to the opposite side of battery 28.

Cover 12 which encloses all of the layers of applicator 10 is made from a flexible conductive plastic material such as a polymer impregnated with carbon or surface metalized plastic. Insulating material 34 fills the space between the side wall of raised portion 14 and the various layers contained therein.

An electrically conductive adhesive material 36 coats the underside of lip 16 so that applicator or device 10 may be placed on and adhere to skin 18 and make good electrical contact.

It will be seen that the above described arrangement in general forms a complete electric circuit from one side of battery 28, cover 12, adhesive material 36, skin 18, microporous membrane 22, liquid reservoir 24, and back to battery 28.

Figure 3:
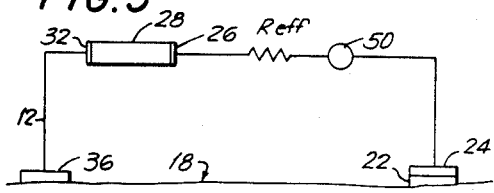
FIG. 3 is a schematic of electrical circuitry incorporated in the embodiment shown in FIGS. 1 and 2 showing an LCD indicator.

For a more particular description of the electrical circuit formed by the arrangement just described, reference is made to FIG. 3 wherein the circuit is shown schematically with numerals corresponding to the structure shown in FIGS. 1 and 2.

Battery 28 is connected through contact 32, cover 12, and adhesive layer 36 to skin 18. The other side of battery 28 is connected electrically through contact 26, liquid reservoir 24 and membrane 22 to skin 18 to complete the circuit. Resistor Reff represents the effective resistance of the complete circuit, including skin 18, the adhesive layer 36, cover 12, battery 28 and its contacts 26 and 32, as well as reservoir 24 and membrane 22. In a system of this type, one of the aims is to establish a very low specific rate of current flow so that the medicament will be deposited slowly over a long period of time. Current flow of down as low as 0.0001 ampere per square centimeter of skin surface below membrane 22 is a typical current which may be selected for the application of a particular drug. Electrical resistance of the skin to current flow is of the order of 6–9 K ohms and is roughly independent of the distance between the points on the skin where electrical contact is made. This is because skin electrical resistance is largely that of resistance to penetration, the current flowing through the fluids of the body in which electrical resistance is very low. Thus, in order to establish current flow at the rate indicated, by Ohm's law, it is seen that total resistance of the circuit using a 1.5 volt battery should be about 360 K ohms for each square centimeter of application. This resistance, the effective resistance, Reff, of the circuit can be built into any one component or combination of components of the circuit shown in FIG. 3, including the battery resistance, electrodes cover material, etc. In addition, if desired, in order to maintain current flow constant over the full period of operation a constant current limiting device can be made integral with and a part of conductor 26, or any other part of the circuit where it is found convenient to do so.

Figure 4:
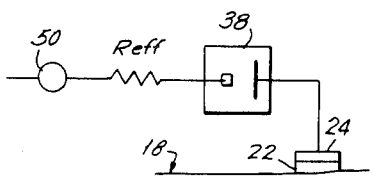
FIG. 4 is an alternative arrangement for the circuit shown in FIG. 3.
Figure 11:
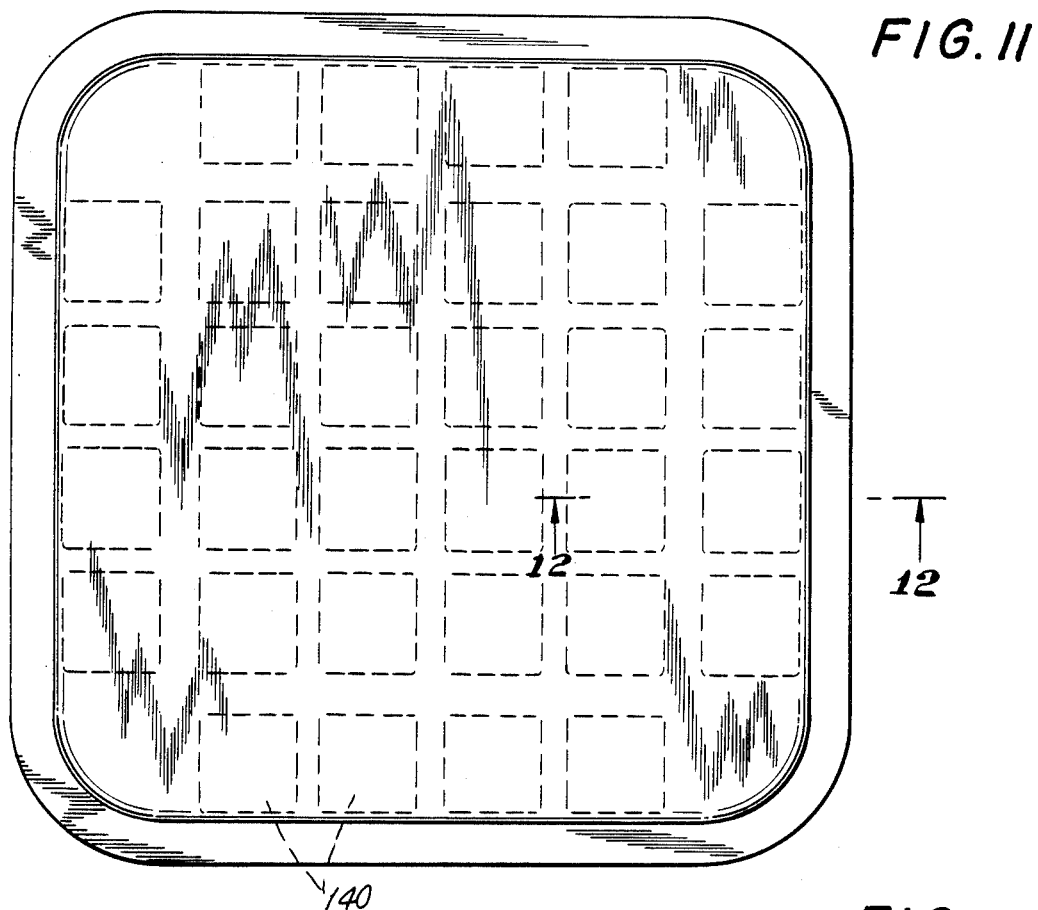
FIG. 11 is a plan view of another embodiment of the applicator wherein separate small patches are employed in the applicator construction.
Figure 12:
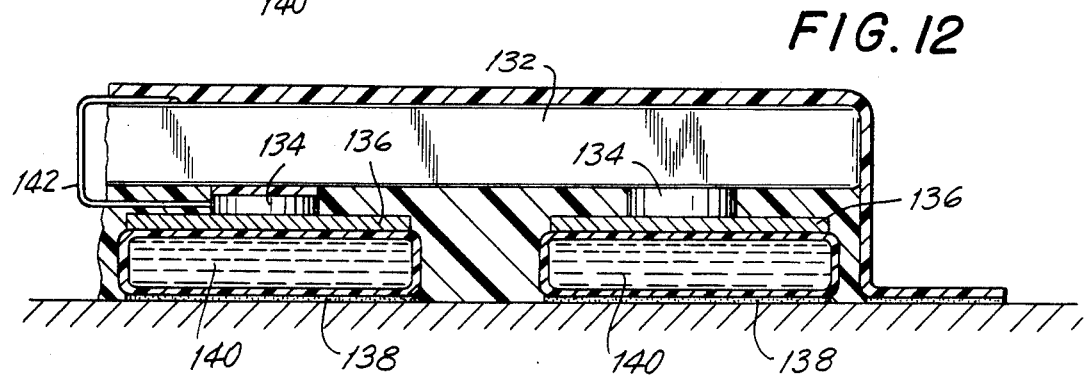
FIG. 12 is a sectional view taken along the line 12—12 of FIG. 11, and showing the applicator on skin.

Furthermore, as indicated schematically in FIG. 4, applicator 10 may be designed to incorporate a provision to insure that the deposit of medicament will cease after a given period of time or after a certain quantity of drug is administered. The termination of current flow can be achieved by using a conventional solid state timer which will cause the current flow to stop and/or restart in a predetermined manner; also the total on time can be controlled by inserting in a circuit an integrating device such as a reverse plating cell 38. Cell 38, as is known in the art, comprises a pair of electrodes on which one is a coating of material to be transferred to the other electrode. When all of the plating material is deposited, after a predetermined period of time based upon the thickness of the original coating has lapsed, or integrated current flow representing the desired quantity of drug to be delivered, there is a large increase in internal resistance resulting in a substantial drop of current flow and an effective halt to drug migration. Such a device can be employed to establish in advance the period of time over which the medicament is to be applied or, as noted above, the quantity of the drug to be delivered. Cell 38 is a relatively high resistance device and could provide for much of the high resistance required for the operation of applicator 10.

Cell 38 may be made a part of contact 32 or be inserted between contact 32 and cover material 14. In addition, provision may be made for current flow to be built up gradually to avoid any shock to the recipient of the drug.

In FIGS. 1–4, there is shown liquid crystal display (LCD) 50 which is incorporated in the structure and circuitry of device 10. LCD 50 is designed so that it will cause a change in the light appearance only at and with the constant prescribed current of device 10. That is, with a completed circuit at such constant current, the prescribed dosage of medicament is being transcutaneously administered to the user, and LCD is light indicating so as to give a positive indication of this drug administration. In the event of (1) a broken circuit, such as a loosening of the conductive lip from the skin surface, (2) a dissipated or faulty battery, or (3) depletion of the medicament, so as to cause a failure of the constant current, the LCD will not show the liquid crystal display change, and the user will be informed that the prescribed drug is not being administered. The user is thus given a clear positive indication that either the drug is being properly administered or the drug is not being properly administered. In the latter event, the user merely removes the device and applies a new device, and upon the new application, the new LCD will be activated.

While the invention has hereinabove been described in the context of an LCD, light emitting diodes (LED) are also within the contemplation of this invention.

With the presence of indicator 50, the complete circuit is formed by skin 18, adhesive layer 36, cover 12, battery 28, indicator 50, contacts 32 and 26 filled reservoir 24, member 22 and resistor Reff.

Figure 5:
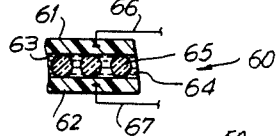
FIG. 5 is an enlarged sectional view of an alternate indicator embodiment.

Referring now to FIG. 5, there is shown a greatly enlarged sectional view of an alternate embodiment 60 for indicator 50. Indicator 60 comprises electroconductive polymeric upper and lower layers 61 and 62, respectively. Layers 61 and 62, in conjunction with non-conductive polymeric end caps (not shown), form a reservoir 63. Upper layer 61 has at least one transparent portion or is fully transparent for purposes hereinafter appearing. An electrchemically conductive phototropic material in the form of a solution or gel 64 is disposed in reservoir 63. A unilayer of silica particulates 65 is disposed in reservoir 63 so as to provide non-conductive spacing for layers 61 and 63.

Electrical leads 66 and 67 are provided to complete the circuit with battery 28 and contact 24, respectively.

Electrochemically phototropic or electrochromic materials will change color or appearance with the passage of the current through the material. Reservoir 63 is filled with such color changing material which is viewable by the user through transparent upper layer 61 of the present device. Suitable electrochemical phototropic materials include, by way of example, those ion change sensitive indicator dyes as disclosed in U.S. Pat. No. 4,013,414, granted Mar. 22, 1977 to Lavalee et al. By providing a highly polar condition in the indicator of the present invention, such ion change sensitive indicator dye color variations would be detected, thereby informing the patient that the medicament is being administered.

A most preferred electrochromic indicator device for use in the present invention electrodes is that disclosed in U.S. Pat. No. 4,066,366, granted Jan. 3, 1978 to Zeller, which disclosure is incorporated herein by reference thereto.

It is also within the contemplation of the present invention that the device's constant current be utilized to effect a change in electromotive force, temperature or other kinetic energy on a chemical and/or dye material which is color-responsive or phototropic with such change, so as to serve as an indicator. Such suitable dye materials are, by way of example, disclosed in U.S. Pat. No. 4,362,645, granted Dec. 7, 1982 to Hof et al.

Applicator 10 may be prepared in advance, in different sizes and shapes, sealed within a plastic pouch, with a protective strip over its exposed side. Different drugs can be incorporated for particular applications, batteries may be varied to meet specific current flow requirements, and of course the electrical orientation of each battery would depend on the particular medicament. In the use of the device, the protective strip is removed and the applicator placed on the skin where desired, such as behind the ear.

Current flow starts immediately along with migration of the drug.

The use of the invention as herein described makes it possible for the first time to provide for drug therapy over an extended period of time with a degree of control and accuracy which heretofore has not been possible or practical. The cost of such therapy using this invention is reduced significantly with the result that extensive use of the invention will have a favorable economic impact on medical care. The indicator now provides a positive degree of assurance to the user not heretofore available in body worn medicament dispensers.

In the embodiment of FIGS. 6–8, there is shown an applicator 70 having an outer cover 72 with a raised portion 74 and a lip 75 along the outer periphery. Within the raised portion 74 is a first layer 76, such as a microporous or semi-permeable membrane through which a drug is delivered by means of electrophoretic and/or electro-osmosis activity. As previously noted, in connection with FIGS. 1–2, this first layer may not be needed, depending upon the nature of the medicament and if it is carried by means of a pad or reservoir type pouch.

The second layer consists of a flexible pouch 78 (or pad or other reservoir) containing the drug. The pouch 78 precludes leakage, but is porous so as to permit drug migrations, be it by means of either or both of said delivery systems noted hereinabove.

The third layer above the pouch reservoir 78 is an extended contact 80 which may be part of one face of the battery 82 which is the next layer. The contact 80 is similar to that of contact 26 described with respect to FIGS. 1–2, and the battery 82 is likewise similar to those previously noted herein.

A further contact 84 above battery 82 is similar to that of contact 80 and same is connected electrically to the opposite side of the battery 82. The cover 72 encloses all layers of the applicator 70 including a third or feedback electrode 86 protruding or extending outwardly beyond the rectangular configuration of the applicator 70, and electrically connected to the contact 84 by means of conductor 88.

Insulating material 90 fills the voids between the side wall of raised portion 74 and the various layers, and also insulates the third or feedback electrode 86 and its wire conductor or lead 88 from coming into contact with any other components of the electrical circuit.

As shown in FIG. 7, contact is made through the skin 90' to the electrically conductive adhesive "electrode" material 92 which coats the underside of lip 75 so that the applicator device 70 is securely adhered in place on the skin 90 with good electrical contact. Such arrangement forms a completed electrical circuit from one side of battery (contact) 82, cover 72, adhesive material 92, skin 90, microporous membrane 76, liquid reservoir 78, and back to battery (contact) 82. The third electrode 86, which feeds back in a loop signal to an amplifier 94, is used as a control probe for sensing drug need. The amplifier's feedback could cause the amplifier to oscillate; the frequency of oscillation and the duty cycle of the oscillations could be independently adjusted as desired or be under the control of the sensing control flow. Such electrode or probe is suitably a conventional type which is, for example, ion-responsive and is provided with appropriate enzymes adhered on its surface 87 for sensing a specified chemical in the body or blood so as to regulate same. Such chemical may, for example, be sugar, insulin, or any other component which is desired to be sensed so as to determine the need for a particular drug. Thus, with such a simple feedback loop circuit, the amplified signal generated may be used to achieve a demand type drug delivery system, whereby drug dosage is controllable to a certain extent upon demand. It will be appreciated that the enzymes employed are capable of picking up the concentration of certain chemicals in the body which are desired to be controlled. Upon the enzyme sensing and detecting the particular chemical in the body, a charge or signal generated in the electrode probe is further amplified as required in order to provide a control signal to the applicator battery circuit for regulating the drug dosage to the desired level. Of course, it should be apparent that the electrode incorporates some sort of semi-conductor and/or field effect transistor which receives, amplifies and transmits the signal measured by the probe.

In FIG. 9, cover 72' is suitably constructed so as to enable the battery 82' and/or pouch 78' to be inserted into the raised portion 74' at the time of use. Either or both of the ends may form flaps 100 and/or 102 which are suitably provided with appropriate means for opening and closing the flaps. For example, minute hook and loop fasteners (shown only on the flap portions as 104) are merely exemplary of one fastening means, but other adhering means are also within the scope of the invention for enabling one or both flaps to be opened and closed. FIG. 10 simply illustrated an embodiment of the invention wherein the battery pack 110 is extremely mounted. Here, one of the battery terminals 112 is electrically connected to the conductive rim 113, and the other terminal 114 is in electrical contact with the reservoir pouch 116. With this construction, there is no need for any movable flaps, and the battery 110 is simply secured to the applicator 120 by any suitable adhesives at the time of asseblying the battery 110 to the applicator device 120.

Referring now to FIGS. 11–12 and 14–16, the applicator can be made with a plurality of cells or reservoir units 140. Such a type of construction lends itself to greater flexibility and ability of the applicator to conform to the contours of various parts of the body where such applicator package is to be used in the administering of drug dosages. Each cell or unit 140 is suitably surrounded by a non-conductive hydrophobic gel so as to insulate the cells or units 140 from each other. The battery 132 and one of its terminal electrodes is spaced, but electrically connected through a suitable resistor 134 to the layer 136. Between layer 138 and layer 136 is the drug reservoir pouch 140. The other resistor is suitably insulated from the same battery terminal side and is connected by means of a suitable lead 142 to the opposite terminal of the battery. Each cell or reservoir unit 140 exhibits the same structure which forms an overall grid pattern to the flexible applicator which can be made into any desired shape.

As shown in FIGS. 14–16, the shape may be formed by paired halves 150 and 152, as illustrated in FIGS. 14–15, respectively, with both halves together forming a single unitary applicator patch capable of delivering a single unit dosage of drug to one's body.

In an extreme example of a very flexible applicator patch, FIG. 16 shows a unit which forms "petal" like appendages 154 of a flower structure which likewise forms a unitary applicator package. In this embodiment, there are only eight cells or units as compared to the twelve cellular units of FIGS. 15 and the eighteen cells of the embodiment of FIGS. 14, or the thirty-six cells of FIGS. 10–11.

Figure 13:
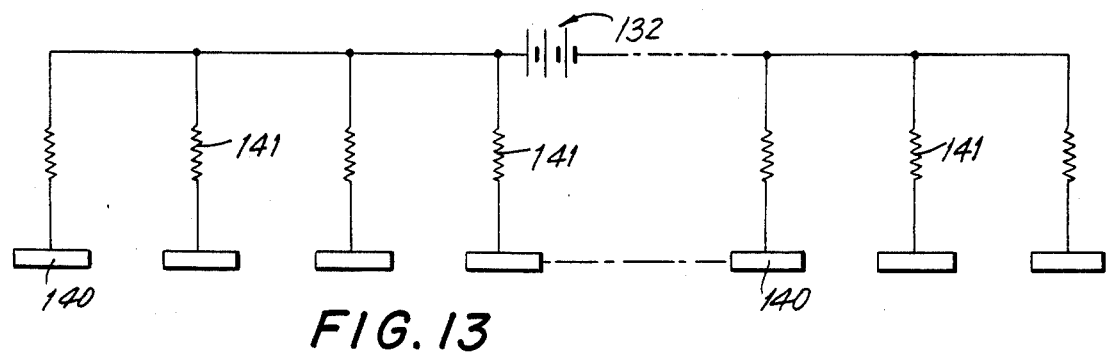
FIG. 13 is an electrical schematic of the circuitry for the applicator illustrated in FIGS. 11-12, and FIGS. 14-16 are plan views of further modifications of the applicator of FIGS. 11-12.

Schematically, the electrical circuits for these applicator packages are all the same, and thus is suitably shown in FIG. 13. As shown therein, the cells 140 form parallel circuits with suitable current regulating devices, such as constant current diodes, operational amplifiers or resistors 141 in series with each cell 140.

The present invention is further illustrated by the following tables illustrating examples which represent test data obtained from preclinical applicator patch models sized approximately 3"×4" and comprising a drug reservoir and a self-contained battery connected by wire to a resistor in series for maintenance of a constant current. The tests consisted of evaluation of serum levels of the drug TROBICIN at various time intervals such as 0,1, 2, 4, etc. hours after continuous application of the device, in both rabbits and dogs.

The animal skins were shaved of fur to expose the skin and to a size to receive the applicator patches, and serum levels were analyzed for the Tobramycin using a radio immuno assay kit. Some of the tests were conducted with TROBICIN solution of different pH.

In each of the experiments, the TROBICIN concentration was equal to 4 gm/37 ml (in solution with distilled or sterile water, which solution was equally applied to the positive and negative electrodes of the patches).

TABLE 1

Transdermal Administration of TROBICIN in Rabbits

| Time | Rabbits Control (No Power - Drug in Patch) | | |
|---|---|---|---|
| | 1 | 2 | 3 |
| | Trobramycin Serum Levels (ug/ml) | | |
| 0 | 0 | 0 | 0 |
| 2 | 0 | 0 | 0.29 |
| 4 | 0 | 0.72 | 0.74 |
| 6 | — | | |

TABLE 2

Transdermal Administration of TROBICIN in Dogs.

| Time | Dogs | |
|---|---|---|
| | I | II |
| | Trobramycin Serum Levels (ug/ml) | |
| 0 | 0.00 ug/ml | 0.00 ug/ml |
| 1 | 0.13 | 0.47 |
| 2 | 0.00 | 0.17 |
| 4 | 0.25 | 0.25 |
| 6 | 0 31 | 0.20 |

Additional experiments were conducted on rabbits with the drugs testosterone and aspirin.

TABLE 3

Transdermal Administration of Testosterone (radio-actively tagged) in Rabbits

| Rabbits (Average of 15 Rabbits) Hours | 0 | 1 | 2 | 3 | 6 |
|---|---|---|---|---|---|
| DPM (Disintegration per minute) | 0 | 27 | 69 | 73 | 98 |

A control group was also tested with like patches and radio-tagged testosterone, but no power was employed and no measured results were recorded.

Pooled urine samples were also taken for each animal, and the weighted average of the DPM for all animals over the period of the above-noted test was 41 DPM.

TABLE 4

Transdermal Administration of Aspirin in Rabbits.

| Rabbits (Average of 5 Rabbits) Hours | 0 | 1 | 2 | 3 | 4 |
|---|---|---|---|---|---|
| Milligrams/ liter | 0 | 17 | 20 | 20 | 22 |

Although these results are representative of initial laboratory experiments, the protocol and procedures do not reflect an optimization of the device's capabilities. These tests do clearly verify the proof of principle in that the results of the serum RIA assays demonstrate that the devices did transdermally deliver Trobicin into the systemic system; and that in the case of both animals, Trobramycin was introduced into their systemic system by means of the activity of the patch.

In two other series of experiments by the inventor on himself using Trobramycin, the serum levels registered readings of 0.3 and 0.5 after 2 and 3 hours, respectively: and readings of 0.4, 0.12 and 0.5 after 1, 2 and 3 hours, respectively.

It should be noted that with respect to the transdermal delivery of a drug to the systemic system, among the varying factors electrophoresis as well as electro-osmosis may be of more or lesser significance depending upon a particular medicament and the desired rate of delivery.

It will be appreciated that each medicament exhibits an optimum mobility at a predetermined pH. The passage of electric current will induce a pH in the solution. This change could be beneficial or detrimental in which case a buffering agent is used to stabilize the desired pH at the optimal level.

The buffering agent or agents have a range of activity (e.g. a pH from say 4 to 5) and the medicament solution prior to the application of the patch could be at a pH which will assure long storage and shelf life, but not be the optimum pH for high drug mobility (drug delivery). The beginning of the current flow during the beginning of the use of the patch could start shifting or changing the pH into the range at which the buffer exhibits its buffering action. As the current continues its action on the solution, a predetermined point could be reached at which the buffer(s) is exhausted, thus reducing the medicament's mobility thereby terminating the drug delivery.

As shown in FIG. 13, there are a plurality of individual drug reservoirs, each one having its own current-/timer solid state regulator. Such a construction allows a simultaneous or sequential delivery of drugs which cannot be mixed with each other and/or systemically delivered at the same time due to the possibility of mutual chemical reactions. Also, it is well known that certain drugs lose their chemical effectiveness if they are mixed with other drugs.

The electro-osmotic transfer or delivery of medicament always takes place at the positive electrode and the electrophoretic phenomena of medicament ion transport into the body is determined by the medicament's ion's polarity, i.e., it could take place at either electrode (negative or positive). If a drug is iontrophoretically delivered by the negative electrode, the same drug could be delivered at the same time by the positive electrode by employing electro-osmosis.

I claim:

1. A transdermal drug applicator for application to the body for migration of medicament through the skin to the blood stream of a patient comprising:

reservoir means containing at least one medicament, battery means for supplying a current to said applicator and being close to said reservoir means for charging/driving the medicament, means for covering comprising an electrically conductive material for partially enclosing at least said reservoir means leaving the side of said reservoir means opposite that of said battery means exposed for contacting said skin, means for electrically connecting the battery means to the cover means, said cover means having lip means for making contact with said skin when mounted on said skin leaving at least said reservoir means substantially fully enclosed, an electrically conductive adhesive material coating disposed on a side of said lip means in contact with the skin when in use, and a sensing electrode and circuit means in a feedback loop mounted on said skin when in use and connected with said electrical circuit for sensing a predetermined chemical in said body and providing a control signal for regulating drug dosage at a desired level, said applicator being generally conformable to the body contour of said patient, whereby when said applicator is adhered to and mounted on said skin a complete electrical circuit through said skin is formed and a medicament in said reservoir means migrates out of said reservoir means and through said skin into the blood stream of said patient, due to the mass transfer activity attributed to at least one phenomena selected from the group consisting of electrophoresis and electro-osmosis.

2. The transdermal drug applicator of claim 1, in which said reservoir means is made from a microporous material whereby said medicament provides an electrical path therethrough.

3. The transdermal drug applicator of claim 2, said circuit having means to maintain constant current flow during the period said medicament is being delivered.

4. The transdermal drug applicator of claim 3, wherein said circuit having means to terminate deposition of said medicament after a predetermined quantity of medicament is delivered.

5. The transdermal drug applicator of claim 1, including a plurality of reservoir means forming separate cell-like reservoirs for said medicament, and each said reservoir cell embodies the same structural layered elements so as to individually charge said medicament by said battery means for causing the migration of said medicament in said reservoir cells through said skin and into the patient's blood stream.

6. The transdermal drug applicator of claim 5, wherein said applicator is divided into a plurality of sections, each with battery means, and said sections being connected together at least at one point, whereby said applicator may be conformable to said body contours.

7. The transdermal drug applicator of claim 6, including parallel electrical circuit paths for the electrical circuit of said applicator.

8. The transdermal drug applicator of claim 6, wherein said sections are generally all equal in size and shape.

9. The transdermal drug applicator of claim 8, wherein each said section is provided with at least one reservoir cell.

10. The transdermal drug applicator of claim 9, wherein a plurality of reservoir cells form each said section and the number of reservoir cells of said sections are the same.

11. The transdermal drug applicator of claim 10, wherein the shape of each reservoir cell is the same.

12. The transdermal drug applicator of claim 10, wherein the shapes of said reservoir cells are not all the same.

13. The transdermal drug applicator of claim 1, wherein said extra electrode is enclosed by said cover means and is disposed at said lip means.

14. The transdermal drug applicator of claim 13, wherein said extra electrode comprising a probe having a predetermined ion specific electrode or enzyme coating on the surface of said electrode portion which is in contact with the skin of said patient.

15. The transdermal drug applicator of claim 14, wherein said extra electrode is disposed in said lip means so as not to electrically interfere with the electrical circuitry of said applicator.

16. The transdermal drug applicator of claim 15, wherein said distance is such that said lip means extends outwardly and protrudes beyond the basic shape and configuration of said applicator.

17. The transdermal drug applicator of claim 1, including one or more buffers in said medicament for maintaining the pH value of the medicament at an optimal level.

18. The transdermal drug applicator of claim 17, wherein the pH of said medicament prior to application of said applicator to one's skin is predetermined at a value which maximizes the shelf life of said drug contained in said applicator, and whereby upon application of said applicator to one's skin the current induced pH change brings the pH within the range of said one or more buffers, thus optimizing drug mobility.

19. The transdermal drug applicator of claim 1, including a plurality of reservoir means.

20. The transdermal drug applicator of claim 19, wherein said applicator transdermally delivers a plurality of drugs and said plurality of reservoir means contain different medicaments, and the delivery of each of said medicaments, is independently controlled by at least one means selected from the group consisting of a current regulating means and a chemical regulating means.

21. The transdermal drug applicator of claim 19, wherein said controlling means is a solid state device pre-programmed for current and time.

22. The transdermal drug applicator of claim 19, further including means for releasing said different medicaments transdermally in a predetermined sequence, 23. The applicator according to claim 1, wherein said feedback loop includes an amplifier, and said feedback loop controls the duration of the on and off periods of the oscillations of said amplifier.

24. The applicator according to claim 23, wherein the duration of the on and off periods of the oscillating amplifier are independently adjustable.

* * * * *